United States Patent
Prabha et al.

(10) Patent No.: US 11,684,638 B2
(45) Date of Patent: Jun. 27, 2023

(54) TARGETED DELIVERY SYSTEM, SYSTEM COMPONENTS, AND METHODS

(71) Applicant: REGENTS OF THE UNIVERSITY OF MINNESOTA, Minneapolis, MN (US)

(72) Inventors: Swayam Prabha, Minneapolis, MN (US); Tanmoy Sadhukha, Minneapolis, MN (US); Buddhadev Layek, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 450 days.

(21) Appl. No.: 15/434,640

(22) Filed: Feb. 16, 2017

(65) Prior Publication Data

US 2017/0232041 A1 Aug. 17, 2017
US 2018/0085403 A9 Mar. 29, 2018

Related U.S. Application Data

(60) Provisional application No. 62/295,557, filed on Feb. 16, 2016.

(51) Int. Cl.
*A61K 35/28* (2015.01)
*C12N 5/00* (2006.01)
*C12N 5/0775* (2010.01)

(52) U.S. Cl.
CPC ............ *A61K 35/28* (2013.01); *C12N 5/0006* (2013.01); *C12N 5/0663* (2013.01)

(58) Field of Classification Search
None
See application file for complete search history.

(56) References Cited

U.S. PATENT DOCUMENTS

| 7,943,330 | B2* | 5/2011 | Wong | G01N 33/582 422/1 |
| 2010/0047892 | A1* | 2/2010 | Laine | C12N 5/0006 435/193 |
| 2011/0002852 | A1* | 1/2011 | Chopp | A01K 67/0271 424/9.1 |
| 2016/0136299 | A1* | 5/2016 | Avila | C07K 16/2893 435/262 |

OTHER PUBLICATIONS

Yhee (Advances in targeting strategies for nanoparticles in cancer imaging and therapy, 2014). (Year: 2014).*
Sadhukha, Glycoengineered Mesenchymal Stem Cells as Potential Theranostic Agents—Therapeutic Nanoparticle Conjugation (1) Apr. 19, 2015. (Year: 2015).*
Layek. Sadhukha, Glycoengineered Mesenchymal Stem Cells as Potential Theranostic Agents—Proecess Optimization (2) Apr. 19, 2015. (Year: 2015).*
Sadhukha, Tanmoy et al. "Nano-engineered mesenchymal stem cells as targeted therapeutic carriers" 2014 J Control Release, 196:243-51. (Year: 2014).*
Gao, "Mesenchymal stem cells: a potential targeted-delivery vehicle for anti-cancer drug, loaded nanoparticles" 2013 Nanomedicine, 9:174-84. (Year: 2013).*
Lee, Sangmin et al. "Chemical tumor-targeting of nanoparticles based on metabolic glycoengineering and click chemistry" Mar. 2014 ACS Nano., 8:2048-63. (Year: 2014).*
Hart, Courtenay et al. "Metabolic labeling and click chemistry detection of glycoprotein markers of mesenchymal stem cell differentiation" 2011 Methods Mol Biol., 698:459-84 (Year: 2011).*
Koo, Heebeom et al. "Bioorthogonal copper-free click chemistry in vivo for tumor-targeted delivery of nanoparticles" 2012 Angew Chern Int Ed Engl., 51:11836-40. (Year: 2012).*
Ning, Xinghai et al. "Visualizing metabolically labeled glycoconjugates of living cells by copper-free and fast huisgen cycloadditions" 2008 Angew Chem Int Ed Engl., 47:2253-5. (Year: 2008).*
Du, Jian et al. "Metabolic glycoengineering: sialic acid and beyond" 2009 Glycobiology, 19:1382-401. (Year: 2009).*
Akimoto, "Umbilical cord blood-derived mesenchymal stem cells inhibit, but adipose tissue-derived mesenchymal stem cells promote, glioblastoma multiforme proliferation" 2013 Stem Cells Dev., 22:1370-86.
Alexis, "Factors affecting the clearance and biodistribution of polymeric nanoparticles" 2008 Mol Pharm., 5:505-15.
Ayuzawa, "Naive human umbilical cord matrix derived stem cells significantly attenuate growth of human breast cancer cells in vitro and in vivo" 2009 Cancer letters, 280:31-7.
Bae, "Targeted drug delivery to tumors: myths, reality and possibility" 2011 J Control Release, 153:198-205.
Baek, "In vitro migration capacity of human adipose tissue-derived mesenchymal stem cells reflects their expression of receptors for chemokines and growth factors" 2011 Exp Mol Med., 43:596-603.
Barua, "Challenges associated with Penetration of Nanoparticles across Cell and Tissue Barriers: A Review of Current Status and Future Prospects" 2014 Nano Today, 9:223-43.
Baskin, "Copper-free click chemistry for dynamic in vivo imaging" 2007 Proc Natl Acad Sci U S A, 104:16793-7.
Best, "Click chemistry and bioorthogonal reactions: unprecedented selectivity in the labeling of biological molecules" 2009 Biochemistry, 48:6571-84.
Bhattacharyya, "Switching the targeting pathways of a therapeutic antibody by nanodesign" 2012 Angew Chem Int Ed Engl., 51:1563-7.

(Continued)

*Primary Examiner* — Nghi V Nguyen
(74) *Attorney, Agent, or Firm* — Mueting Raasch Group

(57) ABSTRACT

A method for targeted delivery of cargo to a target locus in a subject and components of the system. Generally, the method includes administering to the subject a cell that has an artificial saccharide-derived target presented on the surface of the cell, allowing the cell to localize to a target locus in the subject, then administering to the subject an agent that specifically binds to the artificial target. In some embodiments, the agent can include a therapeutic compound. In some embodiments, the agent can include a detectable label. In some of these embodiments, that method can further include detecting the detectable label.

12 Claims, 11 Drawing Sheets
(11 of 11 Drawing Sheet(s) Filed in Color)

(56) References Cited

OTHER PUBLICATIONS

Bianco, "Mesenchymal stem cells: revisiting history, concepts, and assays" 2008 Cell Stem Cell, 2:313-9.
Boxall, "Markers for characterization of bone marrow multipotential stromal cells" 2012 Stem Cells Int., 2012:975871.
Chanda, "Therapeutic potential of adult bone marrow-derived mesenchymal stem cells in prostate cancer bone metastasis" 2009 Clin Cancer Res., 15:7175-85.
Chen, "In vivo tumor targeting and image-guided drug delivery with antibody-conjugated, radiolabeled mesoporous silica nanoparticles" 2013 ACS Nano., 7:9027-39.
Chen, "A tumor-selective biotherapy with prolonged impact on established metastases based on cytokine gene-engineered MSCs" 2008 Mol Ther., 16:749-56.
Cheng, "Nanoparticulate cellular patches for cell-mediated tumoritropic delivery" 2010 ACS Nano., 4:625-31.
Choi, "Use of macrophages to deliver therapeutic and imaging contrast agents to tumors" 2012 Biomaterials, 33:4195-203.
Choi, "A cellular Trojan Horse for delivery of therapeutic nanoparticles into tumors" 2007 Nano Lett., 7:3759-65.
Colter, "Rapid expansion of recycling stem cells in cultures of plastic-adherent cells from human bone marrow" Proc Natl Acad Sci U S A. 2000;97:3213-8.
Dafik, "Fluorination of mammalian cell surfaces via the sialic acid biosynthetic pathway" 2008 Bioorg Med Chem Lett., 18:5945-7.
Dai, "Potential implications of mesenchymal stem cells in cancer therapy" Jun. 2011 Cancer letters, 305(1):8-20.
Doi, "Cytotherapy with naive rat umbilical cord matrix stem cells significantly attenuates growth of murine pancreatic cancer cells and increases survival in syngeneic mice" 2010 Cytotherapy, 12:408-17.
Du, "Metabolic glycoengineering: sialic acid and beyond" 2009 Glycobiology, 19:1382-401.
Gao, "Mesenchymal stem cells: a potential targeted-delivery vehicle for anti-cancer drug, loaded nanoparticles" 2013 Nanomedicine, 9:174-84.
Groshar, "Imaging tumor hypoxia and tumor perfusion" 1993 J Nucl Med., 34:885-8.
Hamada, "Mesenchymal stem cells (MSC) as therapeutic cytoreagents for gene therapy" 2005 Cancer Sci., 96:149-56.
Hart, "Metabolic labeling and click chemistry detection of glycoprotein markers of mesenchymal stem cell differentiation" 2011 Methods Mol Biol., 698:459-84.
In't Anker, "Isolation of mesenchymal stem cells of fetal or maternal origin from human placenta" 2004 Stem Cells, 22:1338-45.
Jensen, "Use of fluorescent probes: their effect on cell biology and limitations" 2012 Anat Rec (Hoboken), 295:2031-6.
Kang, "Cell labeling and tracking method without distorted signals by phagocytosis of macrophages" Feb. 2014 Theranostics, 4:420-31.
Khakoo, "Human mesenchymal stem cells exert potent antitumorigenic effects in a model of Kaposi's sarcoma" 2006 J Exp Med., 203:1235-47.
Kim, "Clinical applications of mesenchymal stem cells" 2013 the Korean journal of internal medicine, 28:387-402.
Koo, "Bioorthogonal copper-free click chemistry in vivo for tumor-targeted delivery of nanoparticles" 2012 Angew Chem Int Ed Engl., 51:11836-40.
Kucerova, "Tumor cell behaviour modulation by mesenchymal stromal cells" 2010 Mol Cancer, 9:129.
Layek, "Glycoengineered mesenchymal stem cells as an enabling platform for two-step targeting of solid tumors" May 2016 *Biomaterials*, 88:97-109.
Lee, "Chemical tumor-targeting of nanoparticles based on metabolic glycoengineering and click chemistry" Mar. 2014 ACS Nano., 8:2048-63.
Loebinger, "Mesenchymal stem cell delivery of TRAIL can eliminate metastatic cancer" May 2009 Cancer Res., 69:4134-42.

Lu, "Single chain anti-c-Met antibody conjugated nanoparticles for in vivo tumor-targeted imaging and drug delivery" 2011 Biomaterials, 32:3265-74.
Lv, "Concise review: the surface markers and identity of human mesenchymal stem cells" Jun. 2014 Stem Cells, 32:1408-19.
Maeda, "The EPR effect for macromolecular drug delivery to solid tumors: Improvement of tumor uptake, lowering of systemic toxicity, and distinct tumor imaging in vivo" 2013 Adv Drug Deliv Rev., 65:71-9.
Maestroni, "Factor(s) from nonmacrophage bone marrow stromal cells inhibit Lewis lung carcinoma and B16 melanoma growth in mice" 1999 Cell Mol Life Sci., 55:663-7.
Mariani, "Clinical applications and biosafety of human adult mesenchymal stem cells" 2012 Curr Pharm Des., 18:1821-45.
McCarthy, "Targeted nanoagents for the detection of cancers" Dec. 2010 Mol Oncol., 4:511-28.
Moghimi, "Long-circulating and target-specific nanoparticles: theory to practice" 2001 Pharmacol Rev., 53:283-318.
Nakamura, "Antitumor effect of genetically engineered mesenchymal stem cells in a rat glioma model" Jul. 2004 Gene Ther., 11:1155-64.
Ngo, "State-selective metabolic labeling of cellular proteins" 2012 ACS Chem Biol., 7:1326-30.
Ning, "Visualizing metabolically labeled glycoconjugates of living cells by copper-free and fast huisgen cycloadditions" 2008 Angew Chem Int Ed Engl., 47:2253-5.
Nouri, "Genetically engineered theranostic mesenchymal stem cells for the evaluation of the anticancer efficacy of enzyme/prodrug systems" 2015 J Control Release, 200:179-87.
Olson, "Vascular permeability factor gene expression in normal and neoplastic human ovaries" 1994 Cancer Res., 54:276-80.
Oswald, "Mesenchymal stem cells can be differentiated into endothelial cells in vitro" 2004 Stem Cells, 22:377-84.
Park, "Engineering mesenchymal stem cells for regenerative medicine and drug delivery" 2015 Methods, 84:3-16.
Park, "Anti-HER2 immunoliposomes: enhanced efficacy attributable to targeted delivery" 2002 Clin Cancer Res., 8:1172-81.
Pendleton, "Mesenchymal stem cells derived from adipose tissue vs bone marrow: in vitro comparison of their tropism towards gliomas" 2013 PloS one, 8:e58198.
Pirollo, "Tumor-targeting nanocomplex delivery of novel tumor suppressor RB94 chemosensitizes bladder carcinoma cells in vitro and in vivo" 2008 Clin Cancer Res., 14:2190-8.
Pittenger, "Multilineage potential of adult human mesenchymal stem cells" 1999 Science, 284:143-7.
Prabaharan, "Gold nanoparticles with a monolayer of doxorubicin-conjugated amphiphilic block copolymer for tumor-targeted drug delivery" 2009 Biomaterials, 30:6065-75.
Roger, "Mesenchymal stem cells as cellular vehicles for delivery of nanoparticles to brain tumors" Nov. 2010 *Biomaterials*, 31:8393-8401.
Sadhukha, "Nano-engineered mesenchymal stem cells as targeted therapeutic carriers" 2014 J Control Release, 196:243-51.
Sadhukha, Glycoengineered Mesenchymal Stem Cells as Potential Theranostic Agents—Therapeutic Nanoparticle Conjugation (1) Apr. 19, 2015.
Sadhukha, Glycoengineered Mesenchymal Stem Cells as Potential Theranostic Agents—Therapeutic Nanoparticle Conjugation (2) Apr. 19, 2015.
Sampathkumar, "Metabolic installation of thiols into sialic acid modulates adhesion and stem cell biology" Mar. 2006 Nat Chem Biol., 2:149-52.
Sensebe, "Biodistribution of mesenchymal stem/stromal cells in a preclinical setting" 2013 Stem Cells Int., 2013:678063.
Shah, "Mesenchymal stem cells engineered for cancer therapy" 2012 Adv Drug Deliv Rev., 64:739-48.
Singh, "Nanoparticle-based targeted drug delivery" 2009 Experimental and molecular pathology, 86:215-23.
Song, "Targeted delivery of doxorubicin to breast cancer cells by aptamer functionalized DOTAP/DOPE liposomes" Oct. 2015 Oncol Rep., 34:1953-1960.
Sun, "The roles of mesenchymal stem cells in tumor inflammatory microenvironment" 2014 J Hematol Oncol., 7:14.

(56) References Cited

OTHER PUBLICATIONS

Todd, "Mesenchymal Stem Cells as Vehicles for Targeted Therapies" 2011.
Toti, "Interfacial Activity Assisted Surface Functionalization: A Novel Approach to Incorporate Maleimide Functional Groups and cRGD Peptide on Polymeric Nanoparticles for Targeted Drug Delivery" Aug. 2010 *Mol Pharm* 7:1108-1117.
Valetti, "Peptide-functionalized nanoparticles for selective targeting of pancreatic tumor" 2014 Journal of Controlled Release, 192:29-39.
Wang, "Towards a targeted multi-drug delivery approach to improve therapeutic efficacy in breast cancer" 2010 Expert Opin Drug Deliv., 7:1159-73.
Wang, "Non-genetic engineering of cells for drug delivery and cell-based therapy" Aug. 2015 *Adv Drug Deliv Rev.*, 91:125-140.
Wang, "Clinical applications of mesenchymal stem cells" 2012 J Hematol Oncol., 5:19.
Wei, "Mesenchymal stem cells: a new trend for cell therapy" 2013 Acta Pharmacol Sin., 34:747-54.
Yokoyama, "Endostatin binding to ovarian cancer cells inhibits peritoneal attachment and dissemination" 2007 Cancer Res., 67:10813-22.
Zuk, "Multilineage cells from human adipose tissue: implications for cell-based therapies" 2001 Tissue Eng., 7:211-28.
Wilson et al., "Glycans modify mesenchymal stem cell differentiation to impact on the function of resulting osteoblasts" J Cell Sci., Feb. 15, 2018; 131(4): jcs209452.

* cited by examiner (A)

(B)

TARGETED DELIVERY SYSTEM, SYSTEM COMPONENTS, AND METHODS

CROSS-REFERENCE TO RELATED APPLICATION

This application claims priority to U.S. Provisional Patent Application No. 62/295,557, filed Feb. 16, 2016, which is incorporated herein by reference.

GOVERNMENT FUNDING

This invention was made with government support under EB022558 awarded by the National Institutes of Health. The government has certain rights in the invention.

SUMMARY

This disclosure describes, in one aspect, a cell that has an artificial saccharide-derived target presented on the surface of the cell.

In some embodiments, the cell can be a mesenchymal stem cell.

In some embodiments, the artificial target can include an azide functional group.

In some embodiments, the cell can further include an agent specifically bound to the target. In some of these embodiments, the target can include an azide functional group and the agent can include a group that is reactive with the azide functional group. In one such embodiment, the agent can include dibenzyl cyclooctyne.

In some embodiments, the agent can be bound to a detectable label.

In some embodiments, the agent can be bound to a therapeutic molecule.

In another aspect, this disclosure describes a system for delivery of a cargo to a cellular target. Generally, the system includes a cell that has an artificial saccharide-derived target presented on the surface of the cell, and an agent that specifically binds to the target.

In some embodiments, the agent is bound to a detectable label.

In some embodiments, the agent is bound to a therapeutic compound.

In another aspect, this disclosure describes a method for targeted delivery of cargo to a target locus in a subject. Generally, the method includes administering to the subject a cell that has an artificial saccharide-derived target presented on the surface of the cell, allowing the cell to localize to a target locus in the subject, then administering to the subject an agent that specifically binds to the artificial target.

In some embodiments, the agent can include a therapeutic compound.

In some embodiments, the agent can include a detectable label. In some of these embodiments, that method can further include detecting the detectable label.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawing(s) or photographs(s) will be provided by the Office upon request and payment of the necessary fee.

Bioluminescence and fluorescence images respectively of (i, x) kidneys, (ii, xi) brain, (iii, xii) liver, (iv, xiii) abdominal wall, (v, xiv) spleen, (vi, xv) lungs, (vii, xvi) heart, (viii, xvii) ovarian tumor and (ix, xviii) abdominal tumor are shown. (c) Quantitative fluorescence intensity from the different organs at the end of the study (10 days for control and 28 days for tumor bearing animals). Data represents mean±SD; n=3 for treated and 2 for control; *p<0.05 compared to control ovary.

Figure 6:
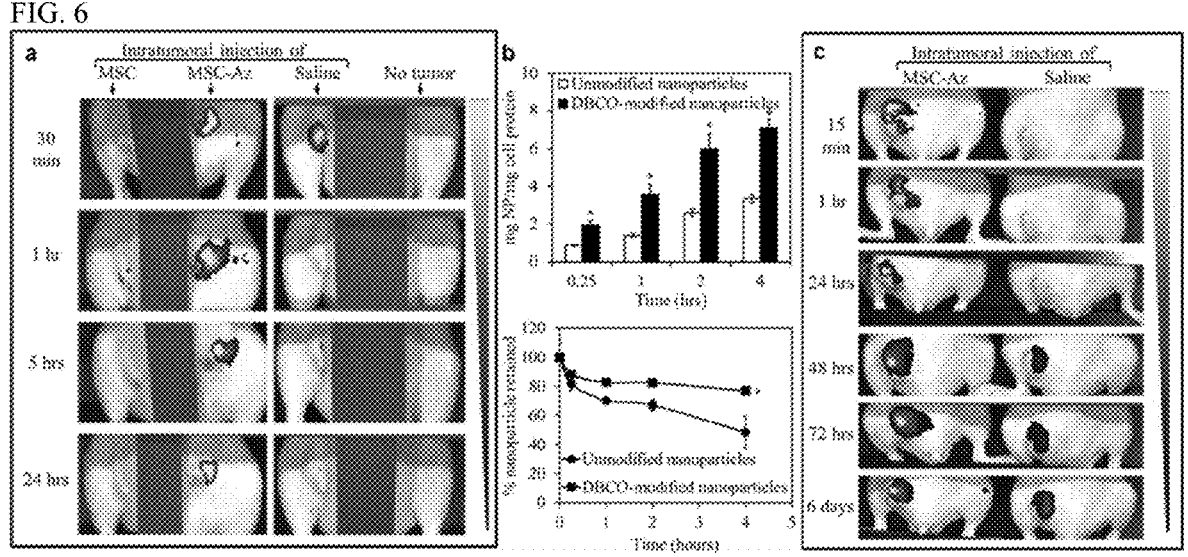

FIG. 6. In vivo click chemistry and two-step targeting using glycoengineered MSCs. Mice bearing subcutaneous A549-Luc tumors were injected intratratumorally with control MSC, MSC-Az or saline. The animals were injected intravenously with (a) DBCO-Cy5.5 or (c) DBCO functionalized PLGA nanoparticles and imaged at different time intervals. The fluorescence intensity in each panel is normalized to the fluorescence from MSC-Az treated tumors. (b) In vitro endocytosis (top) and exocytosis (bottom) of DBCO modified or control polymeric nanoparticles from MSC-Az. Data represents mean±S.D., n=4, *p<0.05 compared to control nanoparticles.

Figure 7:
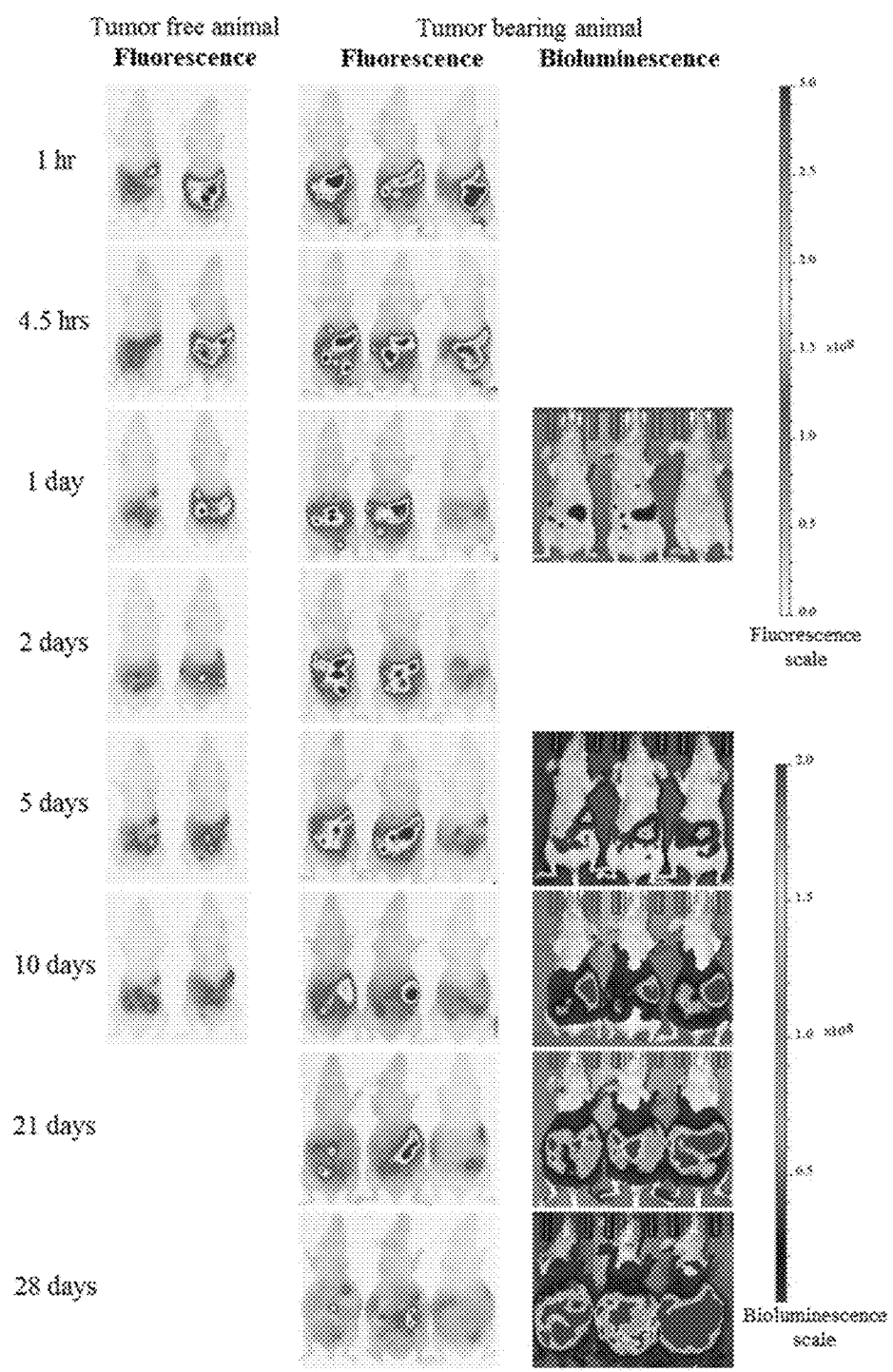

FIG. 7. MA148-Luc ovarian tumor bearing animals were injected with MSC-Cy5.5 intraperitoneally and imaged at different time points. Tumor free animals injected intraperitoneally with MSC-Cy5.5 were used as control. Fluorescence images of all animals at the different time points and bioluminescence images of the tumor bearing mice at 1 day, 5 days, 10 days, 21 days, and 28 days are shown.

Figure 8:
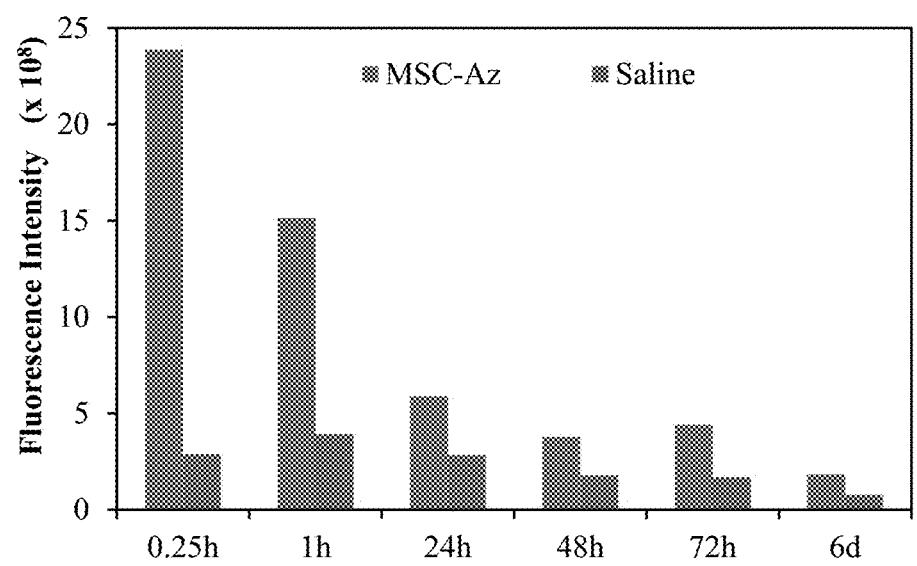

FIG. 8. Mice bearing subcutaneous A549-Luc tumors were injected intratumorally with MSC-Az or saline. The animals were injected intravenously with DBCO functionalized PLGA nanoparticles and imaged at different time intervals. The quantitative fluorescence intensity of nanoparticles from MSC-Az and saline injected tumors are shown.

Figure 9:
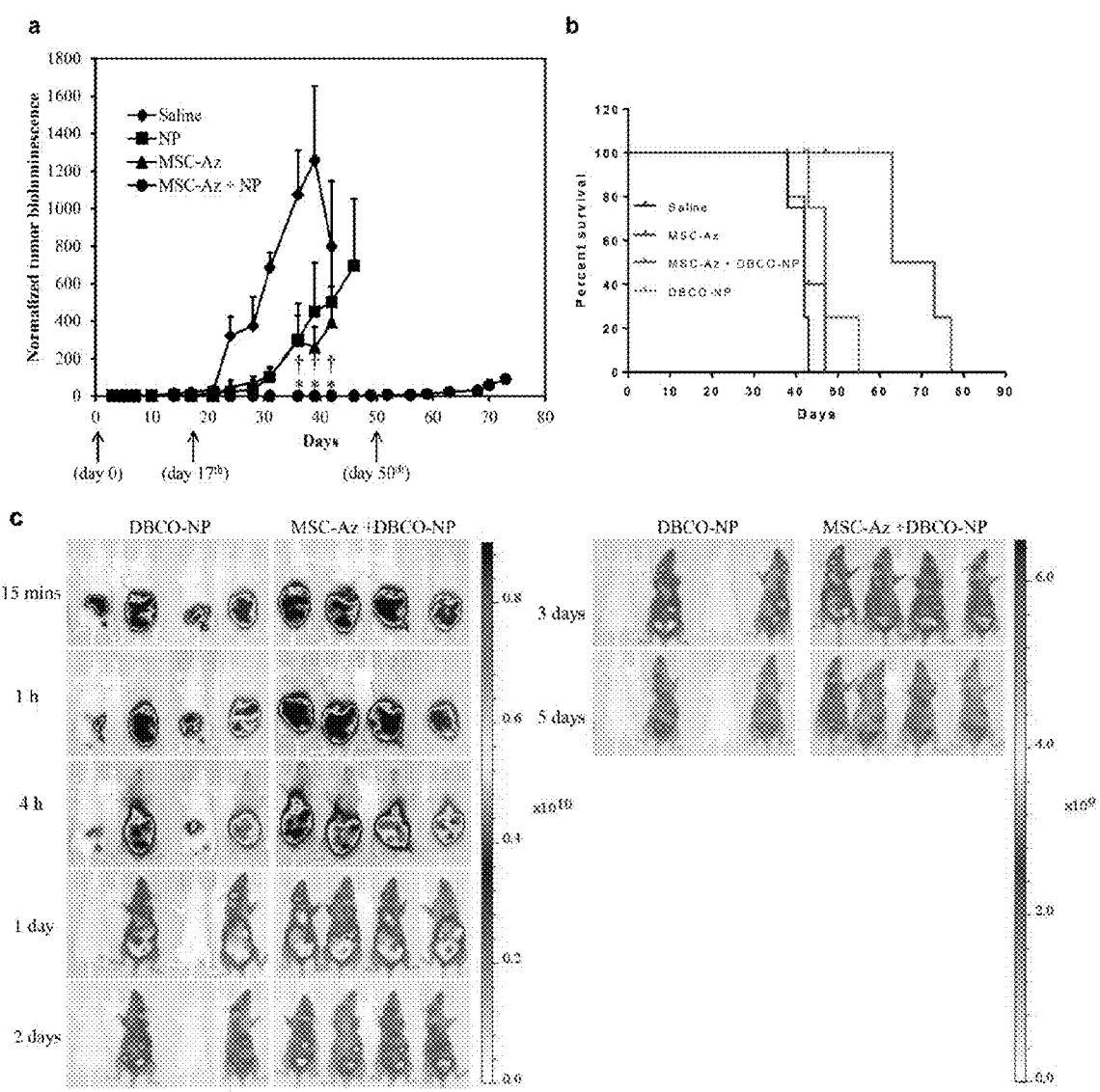

FIG. 9. Antitumor efficacy of the two-step targeting approach. Mice bearing orthotopic ovarian tumors were intraperitoneally injected with saline; $1 \times 10^6$ azide-labeled MSCs (MSC-Az); paclitaxel-loaded, DBCO surface functionalized nanoparticles equivalent to 0.2 mg paclitaxel per animal (DBCO-NP); or $1 \times 10^6$ MSC-Az followed by intraperitoneal injection of DBCO-NP (equivalent to 0.2 mg paclitaxel per animal) (MSC-Az+DBCO-NP). (A) Plot of normalized bioluminescence readings (±SEM; n=4). The bioluminescence of saline group was significantly higher than all three groups from 24 days onwards. '*' indicates significantly different (p<0.05) from MSC-Az and '†' indicates significantly different (p<0.05) from DBCO-NP. (B) Kaplan-Meier survival curves for the different treatment groups: blue line, saline (median survival 42 days); red line, MSC-Az (median survival 42 days); green line, paclitaxel loaded nanoparticles (median survival 51 days); purple line, MSC-Az+NP (median 64 days). Log-rank test of MSC-Az+DBCO-NP and each control group yields p<0.0001 (*).

Figure 10:
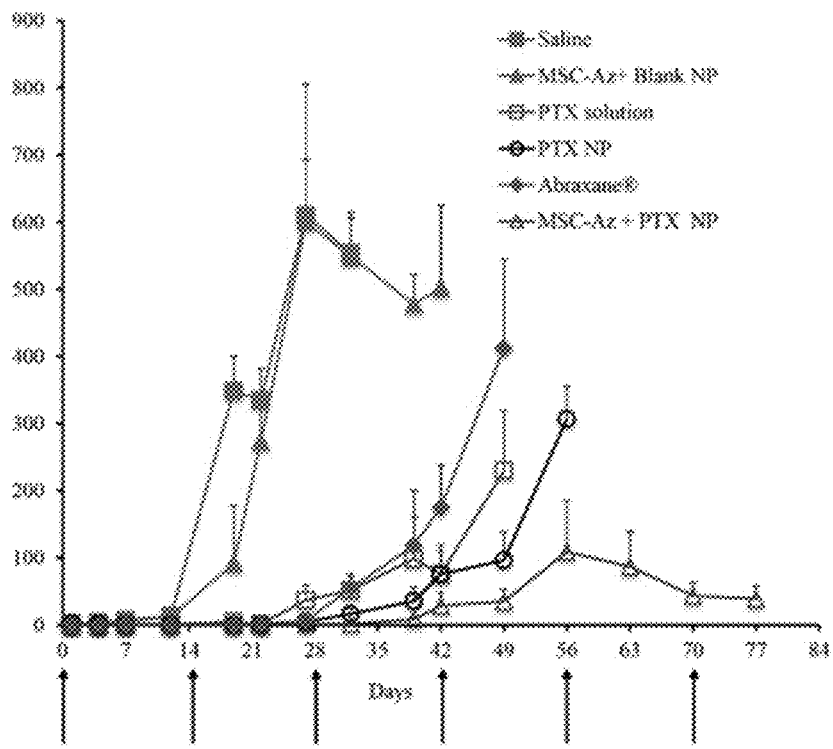
Figure 10:
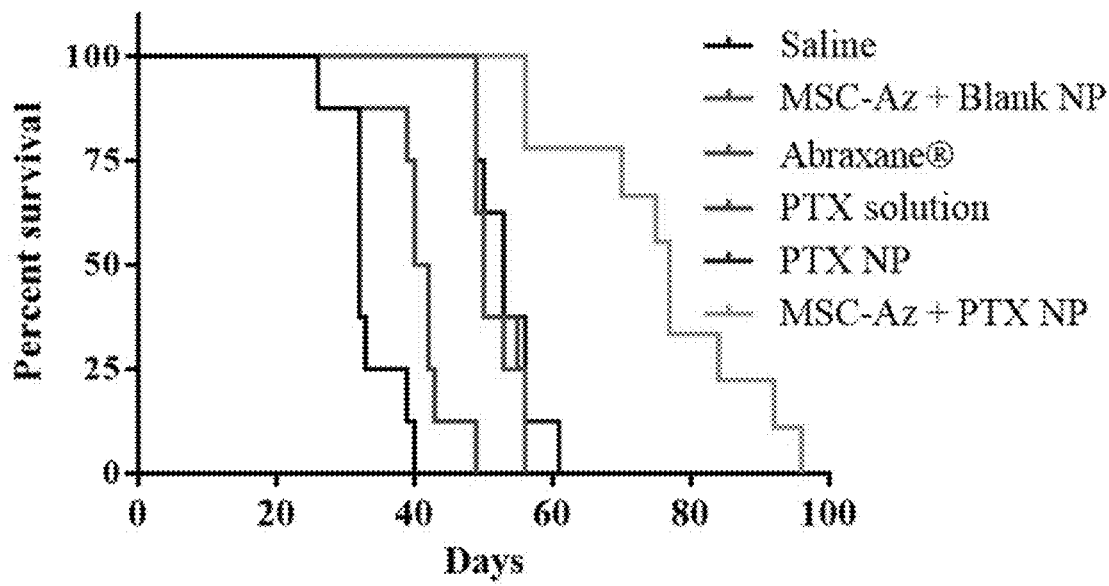

FIG. 10. Antitumor efficacy of glycoengineered MSC pre-incubated with DBCO-functionalized paclitaxel nanoparticles. Mice bearing orthotopic ovarian tumors were intraperitoneally injected with saline; $2 \times 10^6$ azide labeled MSCs pre-incubated with blank nanoparticles (MSC-Az+Blank NP); $2 \times 10^6$ azide labeled MSCs pre-incubated with DBCO functionalized paclitaxel nanoparticles (MSC-Az+PTX NP); paclitaxel solution (PTX solution, Dose equivalent to that used with MSC-Az+PTX NP group), paclitaxel-loaded, DBCO surface functionalized nanoparticles (PTX-NP; Dose equivalent to that used with MSC-Az+PTX NP group); and ABRAXANE (Celgene Corp., Summit, N.J.) (administered on day 0, 4, and 8 at a dose equivalent to 40 mg/kg of paclitaxel) (A) Plot of normalized bioluminescence readings (±SEM; n=9 for MSC-Az+PTX NP group and n=8 for all other groups). (B) Kaplan-Meier survival curves for the different treatment groups; black line, saline (median survival 32 days); red line, MSC-Az+Blank NP (median survival 41 days); brown line, ABRAXANE (median survival 50 days); purple line, PTX solution (median 50 days); blue line, PTX NP (median survival 53 days); pink line, MSC-Az+PTX NP (median survival 77 days). Log-rank test of MSC-Az+PTX-NP and each control group yields p<0.0001 (*).

Figure 11:
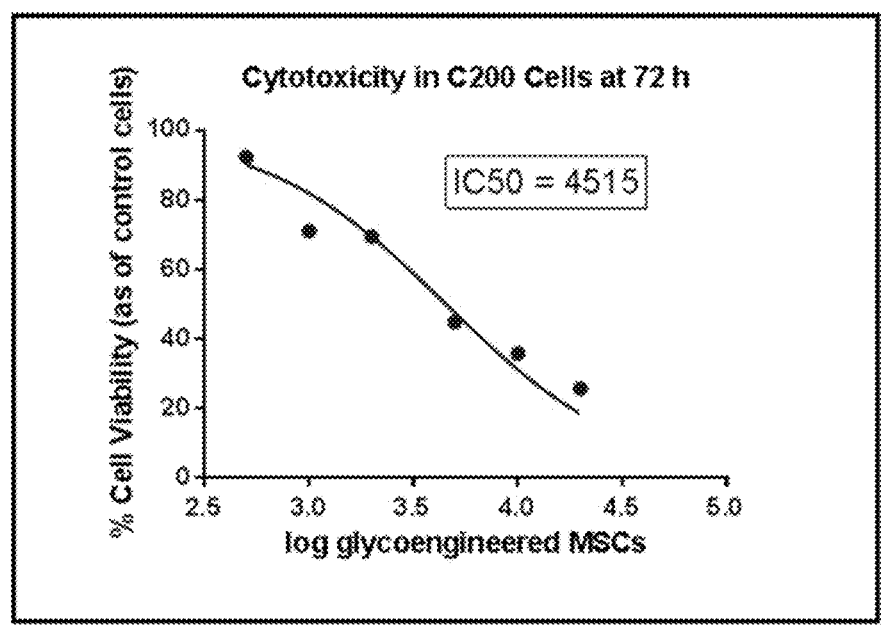

FIG. 11. $IC_{50}$ of glycoengineered MSCs in platinum-resistant C200 ovarian cancer cells in co-culture using TRANSWELL assay (Corning, Inc., Tewksbury, Mass.). The cytotoxic potential of glycoengineered MSCs was determined by co-culturing with C200 cells using a TRANSWELL assay at 72 hours. For cytotoxicity assessment, C200 cells (20,000/well) were seeded in lower chamber of 24 well TRANSWELL plate with different concentrations of glycoengineered MSCs in upper chamber. Approximately 4500 glycoengineered MSCs resulted in 50% inhibition of C200 cells, while the $IC_{50}$ with paclitaxel solution was found to be 4.16 nM. However, when incubated at 1:1 ratio of C200 to glycoengineered-MSCs, 75% cytotoxicity was observed.

DETAILED DESCRIPTION OF ILLUSTRATIVE EMBODIMENTS

Conventional tumor-targeted drug and diagnostic delivery systems can lack selectivity for tumor cells. This disclosure describes a two-step tumor targeting strategy based on mesenchymal stem cells (MSCs), which actively traffic to tumors. The first step involves glycoengineering MSCs to express non-natural azide groups on the surface of the MSCs without affecting the viability or tumor homing properties of the MSCs. Glycoengineered MSCs demonstrated active tumor homing in subcutaneous and orthotopic lung and ovarian tumor models. The second step involves systemic administration of dibenzyl cyclooctyne (DBCO)-labeled fluorophores or nanoparticles to a subject pretreated with the glycoengineered MSCs, which resulted in enhanced tumor accumulation of these agents through bio-orthogonal copper-free click chemistry. These results provide evidence for an MSC-based two-step targeting strategy to improve the tumor specificity of diagnostic agents and drugs, and thus potentially improve the treatment outcomes for patients diagnosed with cancer.

Targeted delivery of diagnostic agents and/or drugs to tumors can improve detection and/or treatment outcomes, respectively. Conventional tumor-targeting strategies can lack selectivity for tumor cells. For example, ligand-based targeting ('active targeting') attempts to exploit tumor cell overexpression of specific membrane proteins by targeting those membrane proteins with an appropriate antibody or ligand. However, many, if not most, of these proteins are also expressed on normal cells. Thus, true tumor-specific targeting is difficult to achieve through targeting of natural membrane proteins. Further, actively targeted delivery systems (such as nanoparticles and liposomes) need to first passively accumulate in the tumor tissue before they can bind with targets on the tumor cell. Passive accumulation of delivery systems in tumors is inefficient—typically, less than 5% of the injected dose reaches the tumor—and is unlikely to be universally applicable to all patients or all delivery systems. Moreover, colloidal systems often do not penetrate effectively into deeper, hypoxic tumor regions because of limited diffusive and convective transport within solid tumors.

In contrast, this disclosure describes a two-step targeting approach that involves introducing synthetic targets in the tumor tissue, followed by the delivery of agents that have high affinity for these targets. Because the targets are not naturally occurring and are not expressed anywhere else, this approach can overcome the lack of tumor specificity seen with conventional ligand-based targeting approaches. As one illustrative embodiment, this disclosure describes the use of azides as model artificial targets. In this exemplary embodiment, non-natural analogs of N-acetyl mannosamine are metabolized by living cells and converted to azido sialic acid expressed on the cell surface without any apparent harm to the host cells. The subsequent reaction of these azide groups with alkynes such as dibenzyl cyclooctyne (DBCO) allows for biorthogonal copper-free "click" chemistry. This azide-alkyne reaction is rapid, selective, produces high yield, and more importantly, is not normally observed in biological systems.

Cancer cells exposed to N-acetyl mannosamine can be visualized by DBCO-based fluorophores. To achieve tumor selectivity, however, the synthetic azides may be made available only in the tumor tissue. In the current studies, mesenchymal stem cells (MSCs) were selected as a model cell population for introducing azide functional groups in the tumor. MSCs possess several distinctive properties that make them an attractive therapeutic and diagnostic tool. For example, MSCs actively traffic to both primary tumors and metastases in response to inflammatory signals. Also, genetically-modified MSCs expressing interleukin (IL)-12 can inhibit the growth of various solid tumors. Thus, the tumoritropic nature of MSCs enables the possibility of active tumor targeting. The results reported in this disclosure demonstrate that glycoengineering of MSCs allows for the expression of unnatural azide groups on their surface.

Further, such glycoengineered MSCs maintain their tumor-tropism and can be targeted using DBCO-based in vivo click chemistry. Thus, the two-step targeting approach described herein allows for efficient tumor targeting of imaging agents and delivery systems in subcutaneous and orthotopic mouse tumor models.

The two-step targeting approach described herein involves introducing non-natural saccharide-derived targets in the tumor tissue, followed by the delivery of agents (e.g., dibenzyl cyclooctyne (DBCO) conjugates) that have high affinity for these artificial targets. As used herein, a non-natural saccharide-derived target refers to a saccharide or polysaccharide molecule that has been modified to contain at least one non-natural functional group—e.g., an azide functional group—that is able to participate in a click chemistry reaction with an agent having high affinity for the saccharide-derived target. While described herein in the context of an exemplary embodiment in which non-natural target includes an azide functional group, the compositions and methods described herein can involve alternative non-natural targets. An exemplary alternative to the azide-cyclooctyne click reaction includes, for example, tetrazine-alkene pairs. A tetrazine-functionalized molecule (e.g., a saccharide) can react with a terminal or strained alkene (functionalized molecules such as vinyl-functionalized molecules), trans-cyclooctene, or methylcyclopropene to form a stable conjugate via a dihydropyrazine moiety.

Thus, while described herein in the context of an exemplary embodiment in which the agent having affinity for the artificial target is DBCO, the compositions and methods described herein can involve alternative non-natural targets, whether an alternative agent that has affinity for an azide functional group or an alternative agent that has affinity for an alternative non-natural target. Accordingly, exemplary alternative agents include, for example, other cycloalkyne-containing moieties (e.g., cyclooctyne, monobenzocyclooctyne, monofluorinated cyclooctyne, difluorinated cyclooctyne, dibenzocyclooctyne, biarylazacyclooctynone, dimethoxyazacyclooctyne), difluorobenzocyclooctyne, bicycle [6.1.0] nonyne, thiacyclooctyne, thiadifluorobenzocyclooctyne, and 3,3,6,6-tetramethylthiacycloheptyne.

Mesenchymal stem cells (MSCs) were used as vehicles for introducing the model artificial target azide functional groups into a tumor. Other cells such as macrophages, T cells, and red blood cells can also be used for this purpose. MSCs possess several properties that make them an attractive therapeutic and diagnostic tool. For example, MSCs do not form teratomas or other uncontrolled growths. They exist in almost all tissues and can be isolated from adult human tissues such as, for example, adipose, bone marrow, muscle, liver, lung, and umbilical cord. MSCs can be expanded and engineered in vitro, and subsequently re-grafted. Moreover, MSCs can home to many solid tumors, rendering them suitable carriers for cancer targeting.

Alternatively, tumor cells can be directly labelled with azide groups via an intravenous injection of precursor-loaded nanoparticles to generate azide groups on tumor tissue. These azide groups then enhance the tumor targeting ability of drug-loaded nanoparticles through copper-free click chemistry during a second intravenous injection. However, the strategy of directly labelling tumor cells may be limited somewhat by nonspecific distribution of nanoparticles after intravenous injection of precursor-loaded nanoparticles—i.e., systemic intravenous delivery will not necessarily result in tumor-specific targeting. Thus, such a strategy may lead to azide groups being generated in healthy tissues, which might contribute to cytotoxicity. In some embodiments, however, the cytotoxicity may be acceptable to achieve the desired level of therapeutic efficacy.

Azide sugar is accepted by the cytidine-5'-monophospho-N-acetylneuraminic acid (CMP-sialic acid) biosynthesis machinery in mammalian cells, leading to the biosynthesis and cell surface expression of azido-sialic acid containing $N_3$-linked glycoproteins. These azide groups are then available for copper-free click chemistry with suitable reaction partners such as DBCO-fluorophores and/or DBCO-containing therapeutic agents. In this study, $Ac_4ManNAz$ was used as the precursor for metabolic glycoengineering because $Ac_4ManNAz$ easily induces the expression of non-natural sialic acids on the cell surface without affecting the host. Similarly, to target azide-bearing sialic acid, DBCO was selected as a biorthogonal chemical moiety due to its high degree of reactivity to azide groups via copper-free click chemistry. Moreover, this reaction does not occur naturally in the human body.

Figure 1:
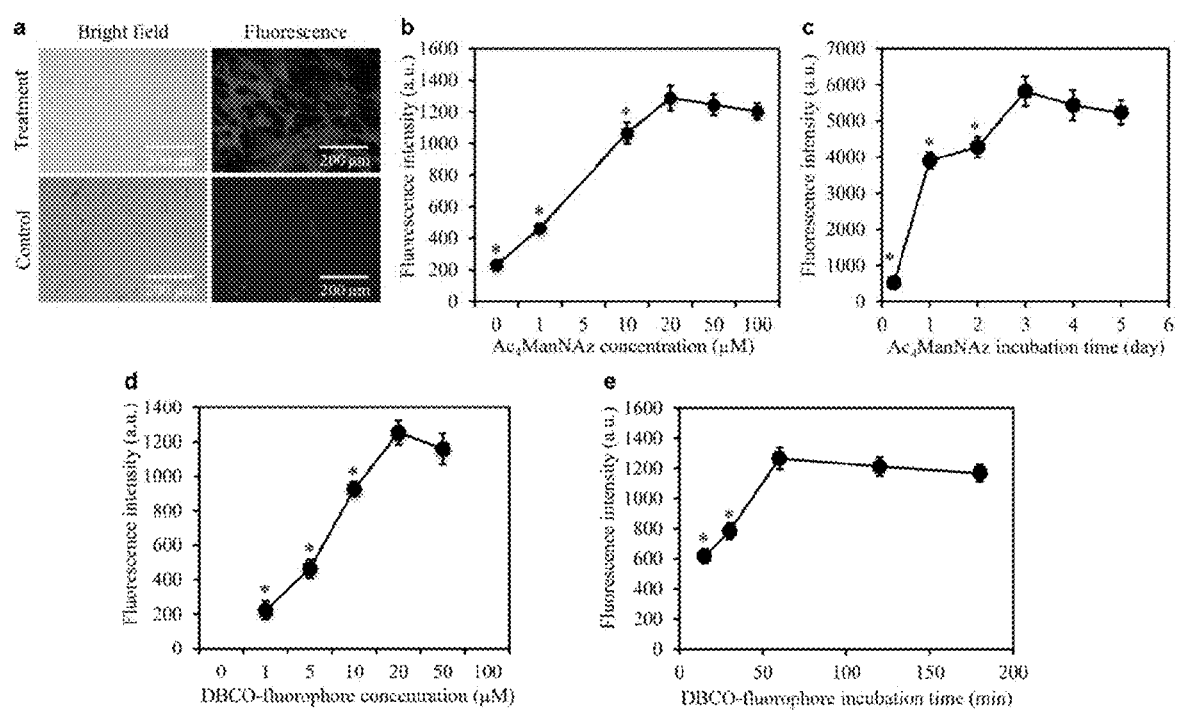
FIG. 1. Glycoengineering parameters. Quantitative analysis of azide groups were performed using a fluorescence spectrophotometer after stained with DBCO-fluorophore. Data represents mean±SD (n=6). (a) Generation of azide groups on the surface of MSCs, (b) Effect of Ac4ManNAz concentrations, $*p<0.01$ compared to 20 µM concentration; (c) Effect of Ac4ManNAz incubation time, $*p<0.01$ compared to three days of incubation; (d) Effect of DBCO-fluorophore concentrations, $*p<0.01$ compared to 20 µM concentration; and (e) Effect of DBCO-fluorophore incubation time, $*p<0.01$ compared to 60 minutes of incubation.

Culturing MSCs in $Ac_4ManNAz$-supplemented media successfully generated targetable azide-bearing sialic acid on their surface, referred to herein as MSC-azide (MSC-Az). Presence of azide groups on the surface of MSCs was confirmed by 'clicking' the cells with DBCO-sulforhodamine B. As can be seen in FIG. 1A, treatment with the DBCO-fluorophore resulted in the labeling of MSC-Az but not control MSCs. The fluorescence intensity of MSC-Az was six-fold higher than control MSCs when treated with DBCO-fluorophore.

Parameters that affect the expression of azide groups on the surface of MSCs and the factors that influence the reactivity of azide groups with DBCO-containing fluorophore were evaluated. To study the effect of $Ac_4ManNAz$ concentration on the cellular expression of azide groups, MSCs were cultured in growth medium supplemented with varying concentrations of $Ac_4ManNAz$. The number of available azide groups on the MSCs surface increased with increasing concentration of $Ac_4ManNAz$ in the culture media (FIG. 1B). MSCs treated with 20 μM $Ac_4ManNAz$ showed the highest expression levels, as measured by fluorophore labeling. Similarly, the number of azide groups on the cell surface increased with increasing duration of incubation of the sugar substrate. The highest surface coverage of azide groups was seen following three days of incubation with $Ac_4ManNAz$ (FIG. 1C). These results suggest that one can saturate the glycan synthetic pathways responsible for the generation of azide groups on the cell surface at either high concentrations (>20 μM) of $Ac_4ManNAz$ or with prolonged incubation (>3 days) with $Ac_4ManNAz$.

To evaluate the concentration and duration of DBCO-fluorophore reaction time, MSC-Az were incubated with 1-50 μM DBCO-fluorophore for 15 minutes to three hours. 20 μM DBCO-fluorophore (FIG. 1D) and a one-hour incubation (FIG. 1E) produced maximum detection of azide group on MSC surface.

Figure 2:
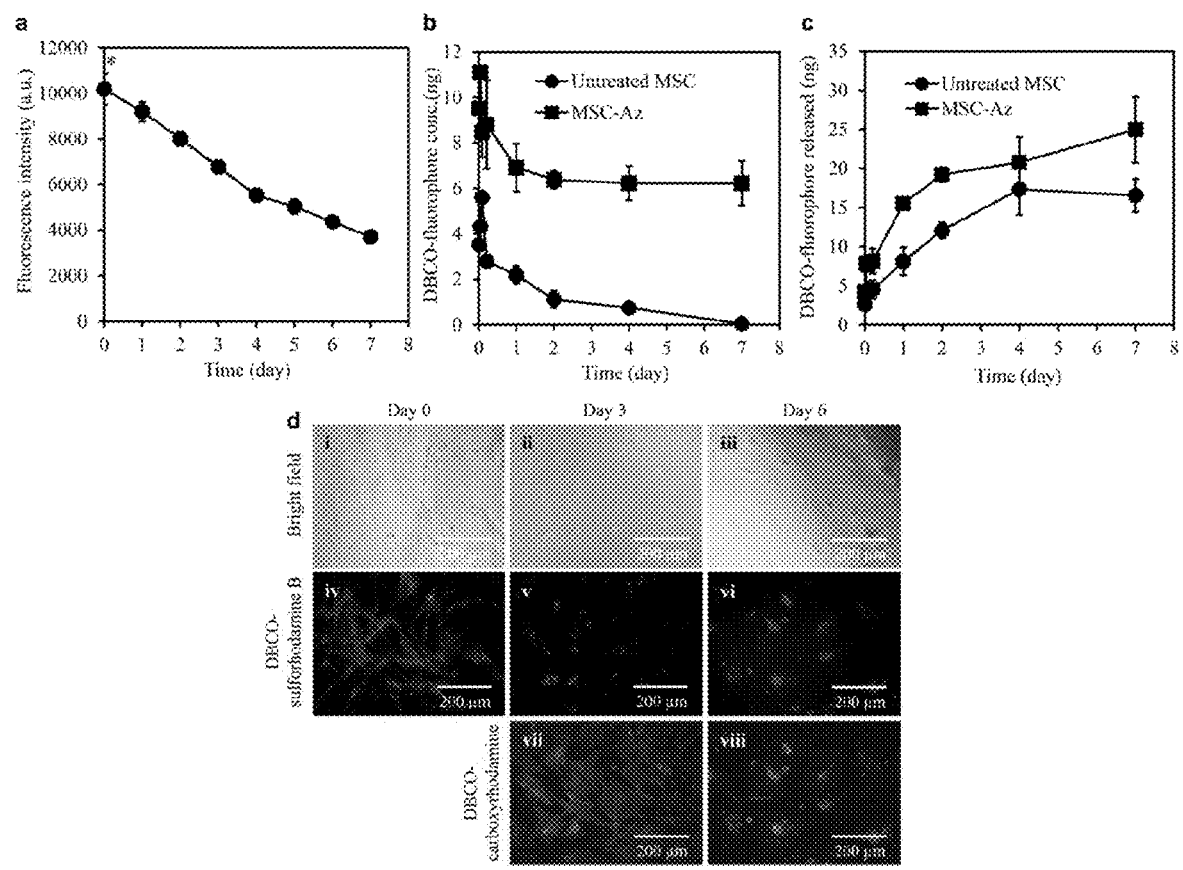
FIG. 2. Stability of azide expression. (a) Retention of azide groups on the MSC cell surface after treatment of 20 µM of $Ac_4ManNAz$ for three days. Data represents mean±SD (n=6), $*p<0.01$ compared to all other time points. MSC-Az was incubated with 20 µM DBCO-carboxyrhodamine for one hour; washed three times with DPBS and (b) dye remaining in cells and (c) dye released in media were measured. Data=Mean±SD; n=3. (d) MSC-Az was transferred to regular media and incubated with 20 µM DBCO-sulforhodamine B (red) on day 0 and 20 µM DBCO-carboxyrhodamine (green) on day 3. Fluorescence images of the DBCO-sulforhodamine B staining of cells (iv-vi) and DBCO-carboxyrhodamine labeled cells (vii, viii) and the corresponding bright-field images (i-iii) are shown.

Long-term stability of the synthetic azide groups on MSC surface facilitates targeting of subsequently delivered DBCO-conjugated therapeutics and/or diagnostic agents. MSC-Az were cultured under normal conditions and the number of available azide groups quantitated using the DBCO-fluorophore labeling technique. The number of available azide groups at the MSC surface gradually reduced with time (FIG. 2A). However, more than one third of the azide groups were still available on the surface of MSCs seven days after the initial treatment.

Similarly, stability of the DBCO-azide conjugate formed through click chemistry can improve effective treatment and/or diagnostic performance. The fate of azide-DBCO conjugate on MSC surface was determined by quantitative estimation of DBCO-fluorophore-associated fluorescence in the cells and in the culture media over time after the initial reaction. The fluorescence intensity of treated cells showed a steady decline over two days, following which the fluorescence levels remained constant over seven days (FIG. 2B). Correspondingly, the amount of dye in the medium increased over two days, beyond when no significant dye release was observed (FIG. 2C).

Click reaction between the azide group on MSC surface and DBCO-fluorophores allowed the immobilization of fluorophores such as Cy5.5 and sulforhodamine B on the MSC surface, resulting in homogeneous bright fluorescence at the cell membrane. One of the concerns with cell-labeling is the loss of the labeling agent from the cells and subsequent non-specific labeling of other cells in the region. For instance, the azide groups can be shed and/or internalized into lysosomes, resulting in the loss of fluorescence signal. In addition, for dyes that stain the cell membrane (e.g., DiI, DiO, DiD and DiR dyes), the dye intensity goes down rapidly because of the fast turnover of cell membrane. As demonstrated in FIG. 2D, the qualitative imaging of the MSC-Az labeled with DBCO-sulforhodamine B (red) showed a homogenous staining of the cell immediately after dye labeling. However, after three days, the dye staining was prominent in the cellular organelles with very little staining of the cell membrane. Treatment with fresh DBCO-carboxyrhodamine (green) resulted in surface staining of MSC-Az with carboxyrhodamine in addition to the pixelated internal staining of sulforhodamine B. Three days post carboxyrhodamine staining, sporadic staining corresponding to both dyes could be observed inside the cells. This suggests that the azide groups constantly cycle to the cell surface, and are available for labeling with clickable groups even several days after the initial glycoengineering. Thus, glycoengineering can overcome some of the drawbacks associated with commonly used cell labeling technologies and could also allow for in vivo labeling and tracking of MSCs.

Figure 3:
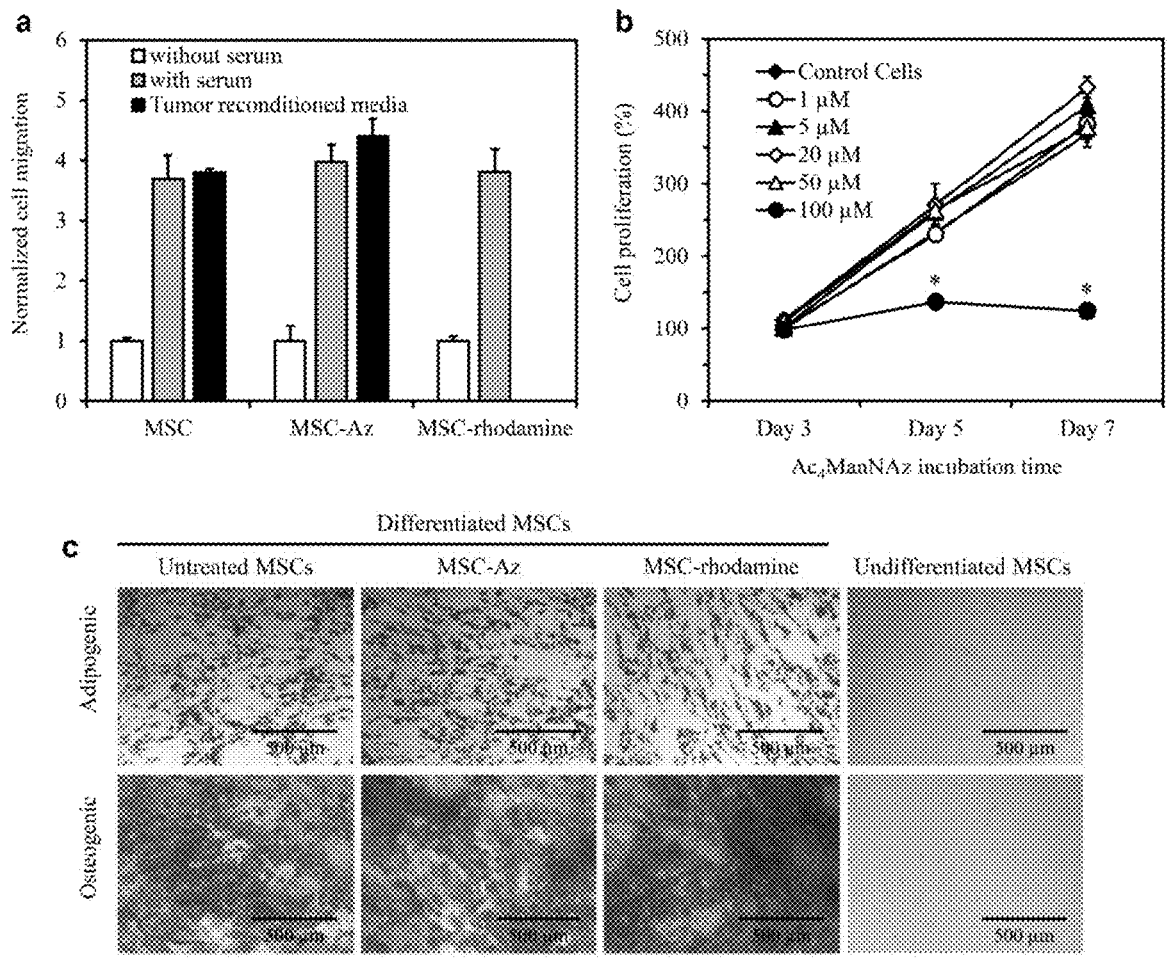
FIG. 3. Effect of glycoengineering on MSC phenotype. (a) Migration potentials of untreated MSC, MSC-Az, and MSC-rhodamine. MSCs were allowed to migrate from a serum-free media towards either serum-free, serum-containing (5% v/v), or tumor-reconditioned media in a TRANSWELL plate (Corning, Inc., Tewksbury, MA). Data represents mean±SD (n=4), (b) Cell proliferation potential of MSCs treated with different concentrations of Ac4ManNaz. Data represents mean±SD (n=6), $*p<0.01$ compared to control; (c) Differentiation potential of glycoengineered MSCs. Control MSCs and glycoengineered MSCs were grown in osteogenic and adipogenic differentiation media for three weeks, after which the cells were fixed and stained to detect differentiation. The staining profile of lipid vacuoles (stained with Oil Red O, characteristic of adipogenic differentiation) and calcium deposits (stained with Alizarin Red, characteristic of osteogenic differentiation) was similar in all groups. Undifferentiated MSCs were stained similarly and used as negative control.

Introducing artificial azide groups on the cell surface can potentially affect the biological responses—e.g., metabolism, cell/cell interaction, and/or migration—of the azide-labelled cells. Therefore, the effect of glycoengineering on migration, differentiation, and proliferation potential of MSCs was evaluated. The TRANSWELL migration assay (Corning, Inc., Tewksbury, Mass.) is often used to study the migratory response of cells to a chemoattractant. The migratory behavior of MSC-Az and MSC-rhodamine was compared to that of untreated MSCs. All the groups showed nearly four-fold higher migration towards serum-containing media and tumor-reconditioned media than towards serum-free media (FIG. 3A). However, there was no significant difference between the migration profile of glycoengineered MSCs and control MSCs, suggesting that the glycoengineering and the subsequent click chemistry do not affect the migratory potential of MSCs. Limited migration was observed in the absence of serum, indicating that MSC migration was highly specific and was not due to the leakage of cells through the membrane.

The long-term viability of glycoengineered MSCs promotes in vivo homing and subsequent targeting with a therapeutic agent and/or diagnostic agent. The viability of glycoengineered MSCs was unaffected by treatment with up to 50 μM $Ac_4ManNAz$ for seven days (FIG. 3B). Cell viability was reduced only at 100 μM $Ac_4ManNAz$ (five times the $Ac_4ManNAz$ concentration at which maximum surface presentation of azide groups occurs) after five days of incubation. This suggests that the process of glycoengineering is not toxic to MSCs.

The multilineage potential of MSCs is commonly studied by monitoring their adipogenic differentiation and osteogenic differentiation under in vitro conditions. As demonstrated in FIG. 3C, there was no difference in the formation of lipid vacuoles (adipogenesis) and deposition of calcium (osteogenesis) in glycoengineered MSCs when compared to that in untreated MSCs. These results suggest that the differentiation potential of MSCs remains unaffected after azide labeling or DBCO conjugation.

In vivo tumor tropism of MSCs enables the use of MSCs for tumor targeting. One study reported a lack of tumor targeting in breast cancer xenografts following intravenous injection of MSCs (Wang et al., 2015, *Adv Drug Deliv Rev.* 91:125-140). However, the fate of MSCs was followed only for a short period of time after intravenous dosing. Thus, it is possible that the study was not conducted long enough to detect the MSCs in tumors. The tumor-tropism of MSCs was studied in lung and ovarian tumor models to confirm that azide modification of MSCs does not affect their in vivo tumor homing capabilities. MSC-carboxyrhodamine demonstrated an initial loss of fluorescence intensity in the first 24 hours post-labeling (FIG. 2B), after which the fluorescence levels remained steady for at least a week. The free DBCO-fluorophore released from the MSC-Az can confound the results of the biodistribution study. To avoid this, MSC-Cy5.5 were administered to mice 24 hours after dye labeling.

Figure 4:
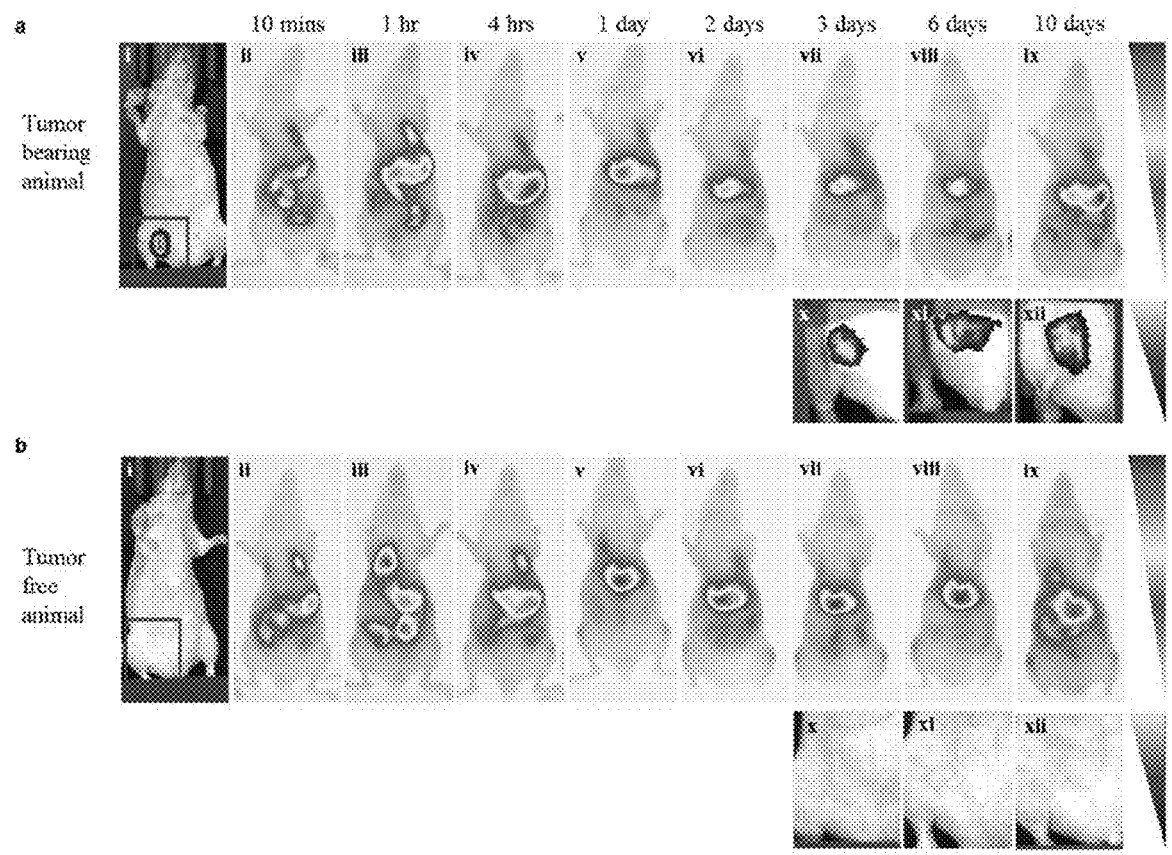
FIG. 4. In vivo tumor-tropism of glycoengineered MSCs (subcutaneous lung tumor xenograft). A549-Luc subcutaneous tumor-bearing (a) and tumor-free (b) animals were injected with MSC-Cy5.5 intravenously and imaged at different time points. Bioluminescence image before MSC-Cy5.5 injection (i) and fluorescence images (ii-xii) are shown. Abdominal region of the mice at 3, 6 and 10 days for (x-xii) are also shown.

Glycoengineered MSCs labeled with DBCO-Cy5.5 dye (MSC-Cy5.5) were dosed intravenously in athymic nude mice bearing subcutaneous A549-Luc lung tumors. Tumor-free animals receiving MSC-Cy5.5 were used as controls. MSC-Az initially accumulated in lungs (first-pass effect) followed by migration to other highly perfused clearance organs such as liver and spleen at earlier time points, irrespective of the tumor status. However, MSC-associated fluorescence could be detected at 72 hours in the subcutaneous tumor tissue, with detectable levels present in the tumor tissues even after 10 days (FIG. 4A). In tumor-free animals, the fluorescence was primarily detected in the clearance organs (e.g., liver and spleen; FIG. 4B). The homing of MSC-Az to subcutaneous tumors provided the initial proof that glycoengineering of MSCs does not affect their in vivo migration and tumor homing properties.

Figure 5:
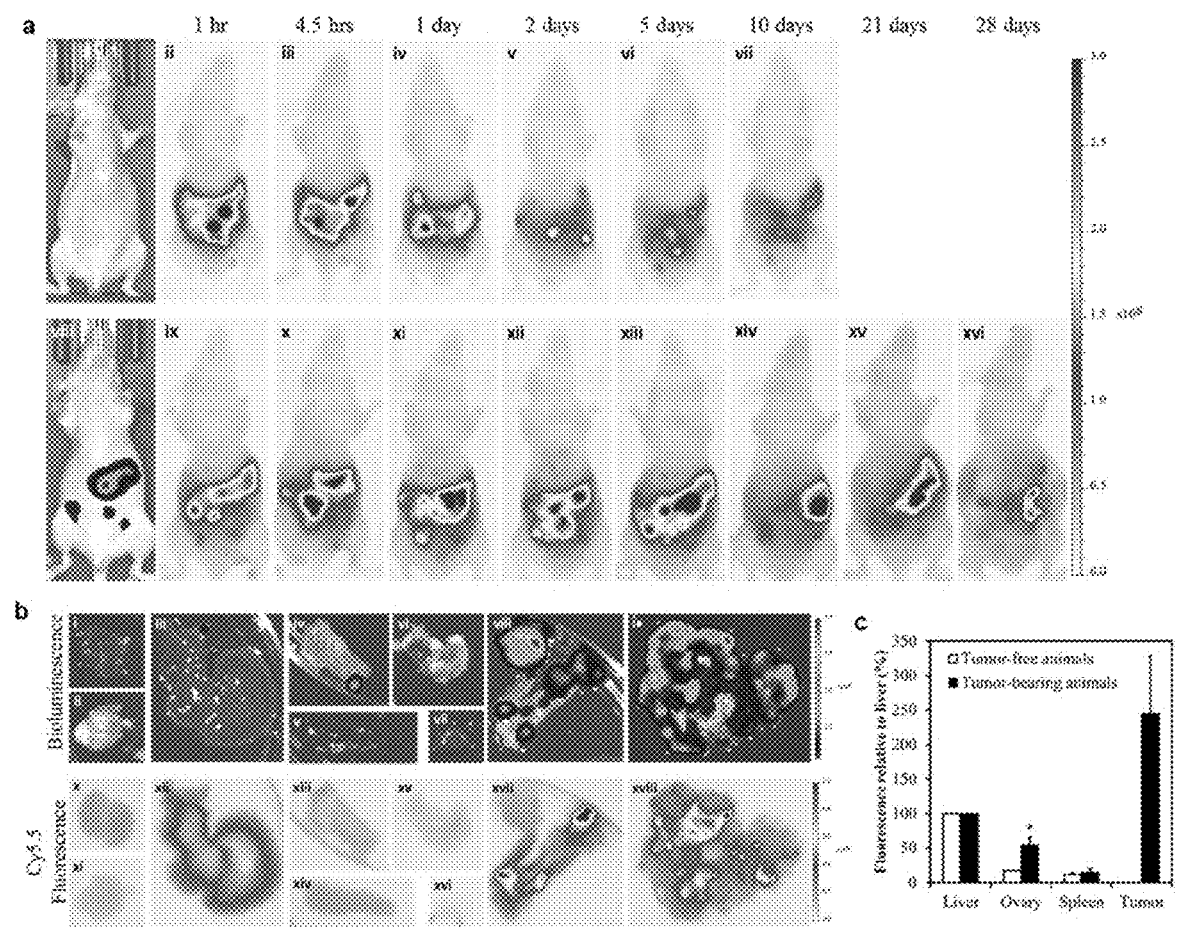
FIG. 5. In vivo tumor-tropism of glycoengineered MSCs (orthotopic ovarian tumor). (a) MA148-Luc ovarian tumor bearing animals were injected with MSC-Cy5.5 intraperitoneally and imaged at different time points. Tumor-free animals injected intraperitoneally with MSC-Cy5.5 were used as control. Representative bioluminescence image (at one day) for (i) tumor free and (viii) tumor bearing animal and representative fluorescence images at different time interval for (ii-vii) control and (viii-xvi) tumor bearing animals is shown. (b) Tissue distribution of glycoengineered MSCs at the end of the study. The animals were euthanized at four weeks and the organs were collected and imaged.

Ovarian tumors were formed by intraperitoneal injection of the MA148-Luc cells in athymic nude mice. The tumors are often found in the abdominal cavity including on the abdominal walls and diaphragm, and also traffic to the ovaries, forming orthotopic ovarian tumors. Intraperitoneal injection of MSC-Cy5.5 in tumor-free mice resulted in initial accumulation of the MSCs in the peritoneal cavity, as shown by high intensity of MSC associated fluorescence in the abdominal region. However, the intensity was significantly reduced after one day (FIG. 5A and FIG. 7). In contrast, MSC-Cy5.5 injected in tumor-bearing animals were found to be associated with the tumors (abdominal cavity) for four weeks after injection (FIG. 5A and FIG. 7). Although there was some loss in intensity with time, MSC-Cy5.5 associated fluorescence signals were still evident at the initial tumor sites three weeks and four weeks after dosing (FIG. 5A and FIG. 7).

Post-euthanasia, abdominal wall, internal organs, and tumors were isolated and imaged for the presence of tumor cells (bioluminescence) and MSC-Cy5.5 (fluorescence). Tumor associated bioluminescence could be detected on the abdominal walls, diaphragm, and on the exterior of all the abdominal organs. Strong MSC-associated fluorescence was detected in the ovaries and the tumor nodules. While some fluorescence was observed in the isolated livers, no distinguishable fluorescence signal was found in the brain, lungs, spleen, kidneys, and heart. These suggests that the MSC-Cy5.5 injected intraperitoneally home to the MA148 tumors and remain associated with tumors for at least four weeks (FIGS. 5B and 5C). Quantitative analysis of fluorescence intensities in isolated tissues demonstrated significantly ($p<0.05$) higher levels of fluorescence in ovaries of MSC-Az treated animals compared to control and in tumors when compared to liver for animals treated with MSC-Az (FIG. 5C).

The use of click chemistry to achieve two-step targeting in vivo is demonstrated in FIG. 6. Two subcutaneous tumors were created in each mouse, with one tumor receiving unmodified MSCs (i.e., MSCs without azide groups) and the other receiving MSC-Az. Intratumoral injection of MSC and MSC-Az eliminates the necessity for tracking their systemic distribution and allows for studying the in vivo clicking of systemically administered DBCO substrate inside the tumor. DBCO-Cy5.5 was dosed intravenously in these mice. Following initial non-specific distribution to both the tumors, DBCO-Cy5.5 cleared rapidly from the tumors that received untreated MSCs. At one hour post dosing, the fluorescent label was detected only in the tumors injected with MSC-Az (FIG. 6A). Interestingly, MSC-Az associated fluorescence was found even at 24 hours post DBCO-Cy5.5 injection.

Use of a delivery system rather than the free drug allows for multivalent interactions and longer residence time in the body. Highly toxic drug payloads can be achieved using polymeric nanoparticles (14% w/w). Therefore, the use of DBCO-azide click chemistry as a way to target polymeric nanoparticles to tumors was evaluated. Surface modification of the poly(lactic-co-glycolic acid) (PLGA) nanoparticles with DBCO groups did not affect their drug carrying capacity (10% w/w as compared to 10.6% w/w for unmodified PLGA nanoparticles). Incubation of DBCO modified nanoparticles with MSC-Az resulted in greater than a two-fold increase in nanoparticle uptake over four hours, compared to control nanoparticles (FIG. 6B). Furthermore, the DBCO modified nanoparticles demonstrated ~30% lower exocytosis compared to control nanoparticles (FIG. 6B).

PLGA nanoparticles surface modified with DBCO groups and labeled with a near-infrared dye were injected intravenously in animals that were pre-treated with an intratumoral injection of MSC-Az. Animals that received intratumoral injection of saline served as a control. Fluorescence associated with nanoparticles was detected in the MSC-Az treated tumors within 15 minutes of nanoparticle injection but not in the control mice. Some DBCO-modified nanoparticles were seen in tumors of saline controls as well after 24 hours, likely due to the passive accumulation of DBCO-modified nanoparticles through enhanced permeation and retention (EPR) effect. Similar to that observed for DBCO-Cy5.5, intravenously injected, DBCO-modified nanoparticles demonstrated enhanced targeting to tumors that received MSC-Az but not to those that received saline (FIG. 6C and FIG. 8), pointing to role of DBCO-azide interactions in tumor targeting of these nanoparticles.

Orthotopic metastatic ovarian tumors were developed in the athymic nude mice by intraperitoneal injection of MA148-Luc cells ($2\times10^6$) in 100 µL of saline. Animals that developed tumors (abdominal bioluminescence more than $1\times10^7$ photons/sec) were randomly divided into different treatment groups. Animals received saline, $1\times10^6$ azide labeled MSC (MSC-Az), paclitaxel loaded nanoparticles equivalent to 0.2 mg per animal (NP), or $1\times10^6$ MSC-Az followed by intraperitoneal injection of nanoparticles (equivalent to 0.2 mg per animal) (MSC-Az+NP). The animals were then re-dosed with the equivalent dose of same formulation at 17 and 50 days.

FIG. 9 shows the utility of the two-step targeting approach for improving the therapeutic efficacy of the model drug paclitaxel, a commonly used anticancer drug, in an orthotopic ovarian cancer model. Treatment involving the two-step targeting approach significantly reduced tumor growth (FIG. 9A; $p<0.05$) and improved survival (FIG. 9B; $p<0.05$) in the group receiving MSC-AZ followed by DBCO nanoparticles. DBCO nanoparticles were retained in the peritoneal cavity longer in the case of animals that first received MSC-Az (FIG. 9C). In contrast, DBCO nanoparticles administered without MSC-Az demonstrated high inter-subject variability in terms of clearance and distribution and were retained at tumor sites for a shorter duration. These results further confirm that two-step targeting strategy leads to prolonged intra-tumoral retention of DBCO surface-functionalized nanoparticles, which is responsible, at least in part, for the observed improved therapeutic efficacy.

FIG. 10 shows the therapeutic efficacy of glycoengineered MSCs pre-incubated with paclitaxel loaded DBCO-nanoparticles. Saline-treated animals were used as positive control. Animals were treated with DBCO-PTX nanoparticles or a control: ABRAXANE (Celgene Corp., Summit, N.J.), PTX solution, or MSC-Az with blank nanoparticles (nanoparticles without drug). Glycoengineered MSCs (MSC-Az+PTX NP) resulted in significant inhibition of tumor growth FIG. 10A, $p<0.0001$) and prolonged animal survival (FIG.

10B). This suggested that in addition to the two-step strategy with glycoengineered MSCs, pre-engineered MSCs provide an alternative therapeutic approach.

This disclosure presents data demonstrating the utility of a two-step targeting approach enabled by glycoengineered MSCs. The results demonstrate that MSC-Az home to tumors and can then be used as anchors for targeting diagnostic agents and/or drug delivery systems. Current active-targeting approaches rely on introduction of targeting moieties such as antibodies, peptides, or aptamers on the surface of delivery systems, which bind to specific membrane proteins over-expressed on tumor cells. However, these targets are not unique to the tumor cell and are present in other healthy tissues, albeit at a lower density, where the delivery system can potentially accumulate. Additionally, most targeting ligands are large molecules, which limit the number of ligand molecules that can be accommodated on the surface of the delivery system. Finally, conjugation of targeting ligand to the surface has to be carefully controlled to prevent loss of binding to the target.

In contrast, the two-step targeting approach described herein creates a synthetic receptor (e.g., an azide functional group) on the surface of cells in the tumor. In certain exemplary embodiments, the targeting moiety is a small molecule that includes a cyclo-octyne group, which can be conjugated to, for example, a dye, an imaging agent, a therapeutic compound, or the surface of a nanocarrier. Thus, this two-step targeting approach can be readily extended to delivery systems, contrast agents, and monoclonal antibodies that are currently being used in the clinic.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

N-azidoacetylmannosamine-tetraacylated (Ac$_4$ManNAz), sulforhodamine B dibenzocyclooctyl (DBCO), carboxyrhodamine 110 DBCO, and Cy5.5 DBCO were purchased from Click Chemistry Tools LLC (Scottsdale, AZ). Ascorbic acid, β-glycerophosphate, dexamethasone, indomethacin, 3-isobutyl-1-methylxanthine, insulin, alizarin red, and oil red O were obtained from Sigma-Aldrich (St. Louis, Mo.). Penicillin/streptomycin and fetal bovine serum were procured from BioExpress Corp. (Kaysville, Utah). Alpha-MEM, RPMI 1640, Dulbecco's phosphate buffered saline (DPBS), and trypsin-EDTA solution were purchased from Invitrogen Corporation (Carlsbad, Calif.). Human mesenchymal stem cells (MSCs) and mesenchymal stem cell media (MSCM) were obtained from ScienCell Research Laboratories (Carlsbad, Calif.). MA148, a human epithelial ovarian carcinoma cell line was established at the University of Minnesota from a patient with stage III epithelial ovarian cyst adenocarcinoma. A549-Luc (Luciferase transfected human lung adenocarcinoma) cells were purchased from PerkinElmer (Waltham, Mass.). D-Luciferin potassium salt was purchased from Gold Biotechnology, Inc. (St. Louis, Mo.). For nanoparticle preparation, ester-terminated 50:50 poly (DL-lactide-co-glycolide) (inherent viscosity: 0.95-1.2 dL/g) was purchased from Durect Corp. (Birmingham, Ala.). Near-infrared dye SDB 5491 was purchased from H.W. Sands, Corp. (Jupiter, Fla.).

Ac$_4$ManNAz and DBCO-fluorophore Parameters

Various Ac$_4$ManNAz concentrations were evaluated as follows. MSCs were seeded onto 96-well plate at a density of 1.5×10$^3$ cells/well in 150 µL of MSCM supplemented with 0, 1 µM, 5 µM, 10 µM, 20 µM, 50 µM, or 100 µM final concentration of Ac$_4$ManNAz. After three days of incubation, the cells were washed twice with DPBS and treated with sulforhodamine B dibenzocyclooctyl (DBCO-sulforhodamine B) (20 µM final concentration) for one hour. Cells were rinsed five times with DPBS and images were taken using a fluorescence microscope. For quantitative analysis, cells treated with Ac$_4$ManNAz were stained with DBCO-carboxyrhodamine and the fluorescence intensity ($\lambda_{ex}$: 485 and $\lambda_{em}$: 528 nm) was measured using plate reader (FLx800 microplate fluorescence reader, BioTek Instruments, Inc., Winooski, Vt., USA).

Similarly, various Ac$_4$ManNAz incubation times were evaluated by culturing MSCs in 20 µM Ac$_4$ManNAz for different incubation times. The cells were treated as before for microscopy or quantitation of available azide groups. The treatments were staggered to perform the final analysis at the same time to maintain the cell number at the time of analysis.

The parameters that affect the in vitro reactivity of azide groups with theranostic agents also were evaluated. MSC-Az prepared by culturing MSCs in 20 µM Ac$_4$ManNAz for three days, were incubated with different concentrations of DBCO-fluorophore (1 µM, 5 µM, 10 µM, 20 µM, and 50 µM) for 15 minutes to three hours and the cellular fluorescence intensity of each sample was quantified by microplate fluorescence reader.

Stability of Azide Groups

To check the azide retention on the cell surface, MSCs were plated into a 96-well plate at a density of 1.5×10$^3$ cells/well in 150 µL of growth media supplemented with 20 µM of Ac$_4$ManNAz. After three days incubation, Ac$_4$ManNAz containing medium was replaced with normal growth media and cultured for 0-7 days. At each time point, cells were incubated with DBCO-carboxyrhodamine for one hour and the fluorescence intensity was measured using a microplate fluorescence reader.

In Vitro Migration Study

The migratory potential of glycoengineered MSCs was compared to untreated MSCs using a 96-TRANSWELL plate (Corning, Inc., Tewksbury, Mass.). MSC-Az with or without DBCO-sulforhodamine B treatment were generated as described above. Untreated MSCs and MSC-Az with and without DBCO-sulforhodamine were serum starved for 24 hours prior to the migration study. Cells were then resuspended in serum-free media and $5 \times 10^3$ untreated or glycoengineered MSCs (in 50 μL media) were placed on the top well of a 96-well TRANSWELL plate (Corning, Inc., Tewksbury, Mass.) separated by an 8.0 μm pore size PET membrane (Corning, Inc., Tewksbury, Mass.). The bottom well was filled with 200 μL of either serum-free medium, 5% serum-containing medium, or tumor-reconditioned medium. Following a migration period of 20 hours at 37° C., both the top and bottom wells were washed with DPBS and calcein AM (1.2 μg/mL) solution in cell dissociation medium was added to the bottom well. After one hour of incubation at 37° C., the cell suspension was transferred to a black-walled 96-well plate and the fluorescence intensity was recorded at 485 nm/520 nm. The numbers of migrated cells were quantified using the standard curves made up with the untreated and glycoengineered cells.

Differentiation Potential of Azide-labeled MSCs

Effect of glycoengineering on adipogenic and osteogenic differentiation abilities of MSCs was performed and compared with untreated MSCs. Both the MSC-Az and MSC-DBCO were generated as described above. Cells were seeded on a 24-well plate at a density of $1 \times 10^4$ cells/well and incubated with adipogenic or osteogenic differentiation media for three weeks (Roger et al., 2010, *Biomaterials* 31:8393-8401). Adipogenic differentiation medium contained alpha-MEM supplemented with 10% FBS, 1% antibiotics, dexamethasone (1 μM), 3-isobutyl-1-methylxanthine (0.5 mM), indomethacin (100 μM), and insulin (10 μg/mL). Osteogenic differentiation media contained alpha-MEM supplemented with 10% FBS, 1% antibiotics, β-glycerophosphate (10 mM), ascorbic acid (100 μM), and dexamethasone (10 nM). Media changes were performed twice weekly. The untreated MSCs incubated under similar conditions were used as the positive control.

For evaluation of adipogenic differentiation, cells were fixed with 4% formalin and stained with oil red O to detect cellular accumulation of neutral lipid vacuoles while alizarin red was used to detect calcium deposits in 70% ethanol fixed cells for the assessment of osteogenic differentiation. MSCs cultured in regular growth medium and stained similarly, served as negative controls. Images were taken at using an inverted microscope at 10× magnification.

Cell Viability Study

To measure in vitro cell viability, MSCs were plated on 24-well plates ($5 \times 10^3$ cells/well) in 500 μL of growth medium supplemented with various concentrations of Ac$_4$ManNAz (1 μM, 5 μM, 10 μM, 20 μM, 50 μM, and 100 μM final concentration). Cell viability was determined by MTS assay at 3 days, 5 days, and 7 days. After incubation for the designated time period, Ac$_4$ManNAz-containing medium was exchanged with 500 μL of fresh growth medium and 100 μL of the MTS/PMS solution was added to each well. Cells were further incubated for one hour at 37° C. and soluble formazan produced by the live cells was measured at 490 nm using a microplate reader. Cells without Ac$_4$ManNAz treatment were used as a control.

Generation of MA148-Luc Cells

Before transduction, the appropriate concentration of puromycin for selecting stably transduced MA148 cells were determined to be 1 μg/mL. Luciferase transduction of MA148 cells were performed using the Firefly Luciferase LENTIFECT Purified Lentiviral Particles (GeneCopoeia, Rockville, Md., USA) according to the manufacturer's protocol. Briefly, $2 \times 10^4$ MA148 cells were plated in each well of a 24-well plate and allowed to attach overnight. On the following day, the cells were treated with viral suspension diluted in 5 μg/mL polybrene in complete medium at the multiplicity of infection of 1. Post transduction, the cells were cultured in medium supplemented with 1 μg/mL puromycin to eliminate the non-transduced cells. After initial selection, the cells were cultured in medium supplemented with 0.3 μg/mL puromycin for one month. Luciferase transfection of the cells was confirmed by bioluminescence imaging of the cells treated with 150 μg/mL D-luciferin.

Animal Studies

All live animal experiments were performed in compliance with a protocol approved by the Institutional Animal Care and Use Committee at the University of Minnesota. Female athymic nude (Crl:NU(NCr)-Foxn1nu) mice and Fox Chase SCID® Beige (CB17.Cg-PrkdcscidLystbg-J/Crl) mice, four to five weeks old, were purchased from Charles River Laboratories (Wilmington, Mass., USA).

Tumor Models

One million A549-Luc human lung adenocarcinoma cells dispersed in 100 μL saline was injected subcutaneously in the abdominal region of SCID® Beige and athymic nude mice to form xenograft lung tumors. Two million MA148-Luc cells dispersed in 100 μL MATRIGEL (Corning, Inc., Tewksbury, Mass.) was injected subcutaneously into the SCID Beige mice for the development of ovarian tumor xenograft. Orthotopic metastatic ovarian tumors were developed in the athymic nude mice by intraperitoneal injection of MA148-Luc cells ($1 \times 10^6$) in 100 μL of saline. After specific intervals, tumor-bearing mice were injected intraperitoneally with 150 mg/kg luciferin and anesthetized (isoflurane) animals were imaged with Xenogen IVIS to confirm tumor growth.

In Vivo Tumor Tropic Properties of MSCs

Tumor tropism of systemically injected MSC-Az was studied in A549-Luc lung tumor model. When the tumor volume reached about 100 mm$^3$, animals received intravenous injection (via tail vein) of $5 \times 10^5$ MSC-Cy5.5 and were imaged at one hour, four hours, one day, two days, three days, five days, and seven days post injection using an IVIS Spectrum live animal imager (Xenogen Corp., Alameda, Calif.). Tumor-free animals that received same dose of MSC-Cy5.5 were used as control. Tumor accumulation of the MSCs was observed based on the intrinsic fluorescence of Cy5.5 ($\lambda_{ex}$: 675 and $\lambda_{em}$: 720 nm).

In vivo tumor tropic characteristics of glycoengineered MSCs were further studied in metastatic MA148-Luc ovarian tumor model. Animals bearing two-week-old tumors were injected intraperitoneally with $2.5 \times 10^5$ MSC-Cy5.5. Anesthetized animals were imaged for MSCs (Cy5.5 associated fluorescence) and tumors (bioluminescence) using an IVIS Spectrum live animal imager (Xenogen Corp., Alameda, Calif.) at various time intervals (one hour, 4.5 hours, one day, two days, five days, 10 days, 21 days, or 28 days). At the end of the study, mice were euthanized and abdomen, brain, liver, kidney, spleen, heart, lungs, reproductive tract, and tumors were harvested for further analysis. The harvested tissues were imaged for the presence of tumor cells (bioluminescence) and glycoengineered MSCs (fluorescence) using Xenogen IVIS Spectrum. Tumor-free mice injected intraperitoneally with MSC-Cy5.5 served as negative controls.

Glycoengineered MSCs for in Vivo Clicking

A549-Luc lung tumors were developed in athymic nude mice such that each animal has two tumors, one on each side of the abdomen. When the tumors reached about 100 mm$^3$, the animals received intratumoral injection ($5 \times 10^5$ cells/100 μL) of control MSCs in one tumor and MSC-Az in the other tumor of the same animal. One hour following MSC injection, 5 µg of DBCO-Cy5.5 in 100 µL DPBS was injected intravenously per mice. DBCO-Cy5.5 binding to MSC-Az was monitored by imaging at different time intervals (0.5 hour, 1 hour, 5 hours, or 24 hours) using an IVIS Spectrum live animal imager (Xenogen Corp., Alameda, Calif.).

Glycoengineered MSCs for Two-Step Targeting

Poly lactic-co-glycolic acid (PLGA) nanoparticles containing an infrared dye (SDB-5491) were prepared by emulsion-solvent evaporation technique and DBCO groups were added on the surface by the interfacial activity assisted surface functionalization technique (Toti et al., 2010, Mol Pharm 7:1108-1117). Uptake and retention of nanoparticles were studied by incubating the MSC-Az with 100 µg/ml unmodified and DBCO-modified nanoparticle for different time intervals (0.25 hour, one hour, two hours, or four hours), washing the cells after four hours, and monitoring the release of nanoparticles from the cells over another four hours. Nanoparticle amount was normalized to the protein content of the cells for analysis of cellular uptake and retention of nanoparticles was calculated based on the percent of cell-associated nanoparticles released into the media.

A549-Luc lung tumors xenografts were developed in athymic nude mice as described before. When the tumor volume reached about 100 mm³, the animal were received intratumoral injection of 2.5×10⁵ MSC-Az in 20 µL DPBS. Control animals received intratumoral injection of saline. One hour following intratumoral injection, 100 µg of DBCO surface functionalized PLGA nanoparticles were injected intravenously in the animals. Fluorescence from the infrared dye ($\lambda_{ex}$: 745 and $\lambda_{em}$: 820 nm) was monitored in the animals at different time periods in an IVIS Spectrum live animal imager (Xenogen Corp., Alameda, Calif.).

Statistical Analysis

Statistical analyses were performed using Student's t-test and one-way ANOVA, followed by Bonferroni-Holm method for comparison between individual groups. A probability level of p<0.05 was considered significant.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A therapeutic delivery system comprising:
    a glycoengineered, undifferentiated mesenchymal stem cell capable of selectively accumulating in a tumor, the glycoengineered, undifferentiated mesenchymal stem cell comprising an artificial surface saccharide, the artificial surface saccharide comprising a reactive functional group; and
    a therapeutic agent comprising a functional group that is reactive with the reactive functional group;
    with the proviso that the glycoengineered stem cell does not comprise a targeting antibody.

2. The therapeutic delivery system of claim 1, wherein the reactive functional group comprises an azide functional group.

3. The therapeutic delivery system of claim 1, wherein the therapeutic agent is bound to the glycoengineered mesenchymal stem cell by reaction of the reactive functional group with the therapeutic agent functional group.

4. The therapeutic delivery system of claim 3, wherein the reactive functional group comprises an azide functional group and the therapeutic agent functional group comprises a group that is reactive with the azide functional group.

5. The therapeutic delivery system of claim 4, wherein the therapeutic agent functional group comprises dibenzyl cyclooctyne.

6. The therapeutic delivery system of claim 1, further comprising a detectable label.

7. The therapeutic delivery system of claim 6, wherein the detectable label is bound to:
    the therapeutic agent, or
    a second artificial surface saccharide.

8. The therapeutic delivery system of claim 1, further comprising a therapeutic agent loaded into the glycoengineered mesenchymal stem cell.

9. A method comprising:
    administering to a subject the glycoengineered mesenchymal stem cell of the therapeutic delivery system of claim 1; and
    administering to the subject the therapeutic agent of the therapeutic delivery system of claim 1.

10. The method of claim 9, wherein the glycoengineered mesenchymal stem cell further comprises a detectable label.

11. The method of claim 10, further comprising detecting the detectable label.

12. The method of claim 9, further comprising allowing the cell to localize to a target locus in the subject.

* * * * *